United States Patent [19]
Huff et al.

[11] Patent Number: 5,288,229
[45] Date of Patent: Feb. 22, 1994

[54] CONVERTIBLE ORTHODONTIC BUCCAL TUBE

[75] Inventors: Stephen M. Huff; William J. Bauer, both of San Diego; Diane K. Bolliger, Ramona, all of Calif.

[73] Assignee: Johnson & Johnson Consumer Products, Inc., Skillman, N.J.

[21] Appl. No.: 1,013

[22] Filed: Jan. 6, 1993

[51] Int. Cl.⁵ .............................................. A61C 3/00
[52] U.S. Cl. .................................................... 433/17
[58] Field of Search ................... 433/8, 11, 13, 16, 17

[56] References Cited

U.S. PATENT DOCUMENTS

| | | | |
|---|---|---|---|
| 3,748,740 | 7/1973 | Wildman | 433/11 |
| 4,551,094 | 11/1985 | Kesling | 433/17 X |
| 4,655,708 | 4/1987 | Fujita | 433/17 X |
| 4,698,017 | 10/1987 | Hanson | 433/11 |
| 4,712,999 | 12/1987 | Rosenberg | 433/11 X |
| 4,786,252 | 11/1988 | Fujita | 433/17 X |
| 4,927,362 | 5/1990 | Snead | 433/17 |
| 5,059,119 | 10/1991 | Snead | 433/17 |

Primary Examiner—Gene Mancene
Assistant Examiner—Nicholas D. Lucchesi
Attorney, Agent, or Firm—Paul A. Coletti

[57] ABSTRACT

A buccal tube contains a rotating integral cover attachable over the archwire slot of the tube.

5 Claims, 1 Drawing Sheet

CONVERTIBLE ORTHODONTIC BUCCAL TUBE

FIELD OF THE INVENTION

This invention relates to orthodontic brackets in general. In particular, this invention relates to orthodontic buccal tubes. Most specifically, this invention relates to orthodontic buccal tubes with an attached cover capable of being opened during an orthodontic procedure.

BACKGROUND OF THE INVENTION

During orthodontic treatment, archwire is placed in the slots of dental brackets that are fixed to the teeth. This archwire is able to guide the teeth toward its desired positions for correct occlusion of the teeth. Typically, the ends of the archwire are held in place by buccal tubes secured to the molars.

Buccal tubes are used by orthodontists during the early stages of the orthodontic treatment; these tubes are similar to the orthodontic brackets in that they have an archwire slot. But, these buccal tubes also have a plate which is capable of closing the slot and forming a typically rectangular tubular opening. The plate is usually removed when desired to open the slot and convert the buccal tube into a dental bracket.

Convertible buccal tubes are used on the molars of younger children who do not yet have second molars. In the early stages of treatment, these buccal tubes serve as anchorage for the ends of the archwire. The cover over the archwire of these buccal tubes in the molars is typically removed before insulation of longer archwires to cover these tubes to dental brackets. Use of these buccal tubes enables the dentist to carry out treatment on the first molars.

Various buccal tubes have been described in the art, and will be provided to the patent office in an information disclosure statement in relation to this patent application.

It has been realized that it is possible for the cover of the archwire slot used in the buccal tubes to be dropped into the mouth during dental procedures. This is particularly true if the dentist is using a typical prying device which is used to remove the buccal tube cap. This represents an inconvenience to the orthodontist as well as to the patient.

SUMMARY OF THE INVENTION

This invention relates to a convertable buccal tube for mounting on a molar, and includes a base. The buccal tube contains a body which has both occlusal and gingival portions. These occlusal and gingival portions separate an archwire slot. A cover is emplacable over the archwire slot and includes a first tab connected to the gingival portion. The tab which connects the cover to the gingival portion is able to rotate about the gingival portion. The tab is permanently held in place therein. The cover is made of a generally metallic but essentially elastically deformable material which enables the cover to be placed over the second tab on the occlusal portion of the bracket. There is optionally a notch which holds the bracket in place over the occlusal portion. Significantly, this bracket is capable of being detained in position over the occlusal portion in order to convert the archwire slot. Optionally, a safety bar may be attached to the buccal tube to prevent clip separation from the bracket body during treatment. This cover not only makes the bracket convertible, but also makes the bracket "reconvertible". This reconvertible feature has been heretofore unknown in the dental field.

DETAILED DESCRIPTION OF THE INVENTION

Figure 1:
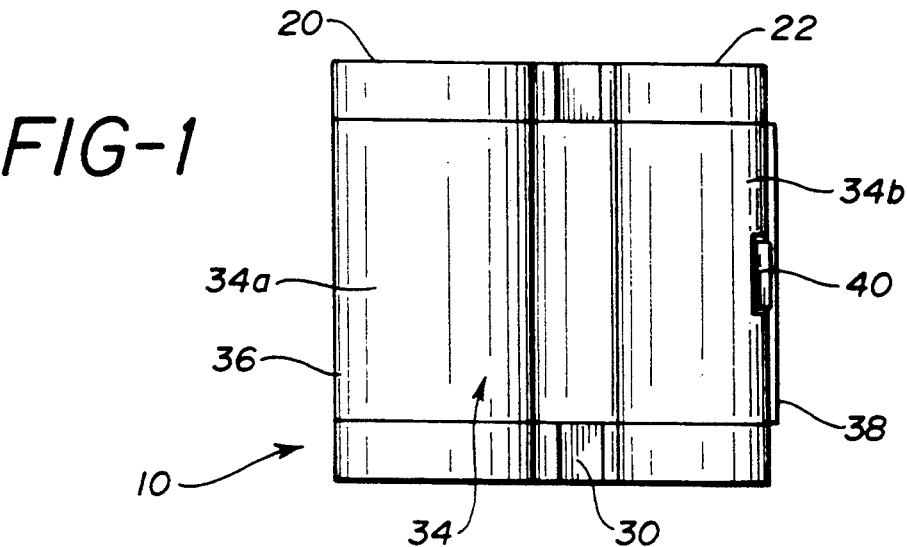
FIG. 1 is an elevational view of the buccal tube of this invention as seen mounted on a tooth.
Figure 2:
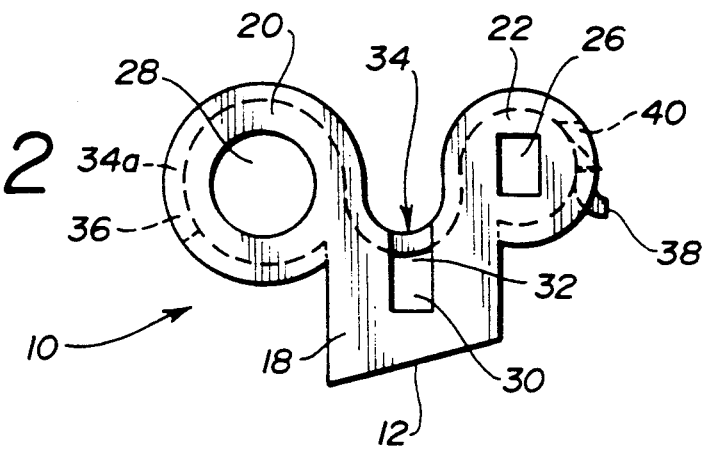
FIG. 2 is a side view of the buccal tube of this invention.
Figure 3:
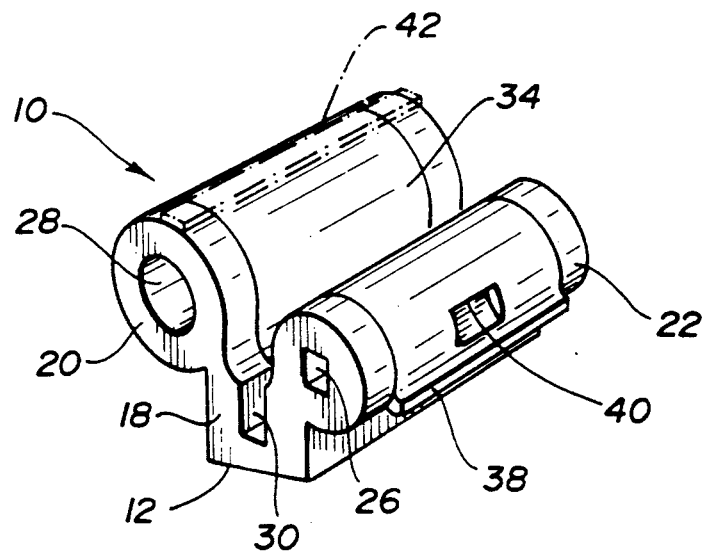
FIG. 3 is a perspective view of the buccal tube of this invention.

An orthodontic buccal tube 10 in accordance with the invention is illustrated in FIGS. 1-3 and includes a base 12 that is attached by conventional means to a lower first molar tooth. The tube 10 also includes a body 18 that is integrally connected to the base 12 and extends outwardly in buccal direction (i.e., toward the cheeks).

The body 18 has an occlusal portion 20 and a gingival portion 22 spaced apart from the occlusal portion 20. The gingival portion 22 may include a mesial hood and a auxiliary archwire slot 26. Occlusal portion 20 contains a facebow slot 28.

An elongated archwire slot 30 extends in a mesial-distal direction across the body 18 between the occlusal portion 20 and the gingival portion 22. The archwire slot 30 has a rectangular cross section that is closely sized to the dimensions of the expected archwire. In this manner, bends or twists placed in the archwire can function to urge the tube 10 and therefore the tooth toward a desired position according to edgewise therapy.

A buccal side 32 of the archwire slot 30 is remote from the base 12, and is closed at cover 34. The cover 34 includes a tab 36 that is integrally connected to the occlusal portion 20, and a second tab 38 that is detainably connected to the gingival portion 22. As illustrated in FIG. 3, the tab 36 permits rotation of cover portion 34a about it, toward tab 38. The tabs 36, 38 may be the same size and have the same cross sectional area when looking in a lingual direction toward the buccal tube 10 as shown in FIG. 1 Detent 40 attached to tab 38 holds cover 34 in place.

Optionally, bar 42 is held over cover 34 so that cover 34 may not detach from tab 36 at portion 34a. Importantly, cover 34 is reliably held in place by detent 40 at portion 34b. To open the cover 34 and convert the buccal tube 10 from the configuration shown in FIG. 2 to the configuration shown in FIG. 3, a prying tool is inserted in the archwire slot 30 and manipulated to bend the tabs 36, 38 outwardly. The cover 34 may thereafter be returned in place by rotating about tab 36.

What is claimed is:

1. A buccal tube for mounting on a tooth comprising:
a base;
a body extending from the base and having spaced apart occlusal and gingival portions, one of said occlusal and gingival portions containing a slot therethrough, said slot capable of accepting a connection for a facebow therein, and the other of said occlusal and gingival portions containing a second archwire slot therethrough, said archwire slot capable of accepting an archwire therein, and said body including a first archwire slot located between the occlusal and gingival portions; and a cover integrally connected to said occlusal portion and a tab attachably connected to said cover, said cover rotatable about said occlusal portion.

2. The buccal tube of claim 1 including a bar holding said cover on said occlusal portion.

3. The buccal tube of claim 1 wherein said tab mates with a detent on said gingival portion.

4. The buccal tube of claim 1 wherein said occlusal portion has a recess for receiving said cover, and wherein said gingival portion has a recess for receiving said tab.

5. The buccal tube of claim 1 wherein said base is integral with said body.

* * * * *